United States Patent
Samour et al.

[11] Patent Number: 5,906,822
[45] Date of Patent: May 25, 1999

[54] CATIONIC FILM-FORMING POLYMER COMPOSITIONS, AND USE THEREOF IN TOPICAL AGENTS DELIVERY SYSTEM AND METHOD OF DELIVERING AGENTS TO THE SKIN

[75] Inventors: Carlos M. Samour, Bedford; Scott F. Krauser, Tyugsboro, both of Mass.

[73] Assignee: MacroChem Corporation, Lexington, Mass.

[21] Appl. No.: 08/937,649

[22] Filed: Sep. 25, 1997

Related U.S. Application Data

[62] Division of application No. 08/771,990, filed as application No. PCT/US96/11001, Jun. 27, 1996.

[51] Int. Cl.$^6$ ............................................. A61K 7/48
[52] U.S. Cl. ..................... 424/401; 424/70.11; 424/78.08
[58] Field of Search ................. 424/401, 78.08, 424/70.11

[56] References Cited

U.S. PATENT DOCUMENTS

| | | | |
|---|---|---|---|
| 3,852,255 | 12/1974 | Bentz et al. | 260/88.7 |
| 3,925,462 | 12/1975 | Graff | 560/26 |
| 4,002,733 | 1/1977 | Degen et al. | 424/59 |
| 4,163,088 | 7/1979 | Kunzel et al. | 525/433 |
| 4,508,916 | 4/1985 | Newell et al. | 556/420 |
| 4,695,645 | 9/1987 | Merger et al. | 560/24 |
| 4,810,582 | 4/1989 | Gould et al. | |
| 4,971,800 | 11/1994 | Chess et al. | 424/449 |
| 5,045,317 | 9/1991 | Chess et al. | 424/401 |
| 5,051,260 | 9/1991 | Chess et al. | 424/449 |
| 5,155,199 | 10/1992 | Hayashi et al. | 528/65 |

FOREIGN PATENT DOCUMENTS 9000066 1/1990 WIPO.

Primary Examiner—Jyothsna Venkat
Attorney, Agent, or Firm—Sherman and Shalloway

[57] ABSTRACT

A mixture of lipophilic and amphiphilic/hydrophilic film-forming polymers of the formula (I)

$$R-(CO)_m Y^1-(CH_2 CHR^1 O)_n-[CONH-Z-NHCO(OCH_2 CHR^2)_{n'}-Y^2-(CH_2 CHR^2 O)_{n''}]_p-CONH-Z-NHCO-(OCH_2 CHR^1)_n-Y^1(CO)_m R \quad (I)$$

where R represents (i) an alkyl, alkenyl or alkaryl group of from 1 to 30 carbon atoms or (ii) a polypropylene oxide group or polybutylene oxide group; $R^1$ and $R^2$, each, independently, represent a hydrogen atom, or a methyl or ethyl group; Z represents a divalent linking hydrocarbyl group; m is 0 or 1; when m=0, $Y^1$ represents O, $NR^3$ or $N^+R^3R^4X^-$ and when m=1 $Y^1$ represents O; $Y^2$ represents O, $NR^3$, $N^+R^3R^4X^-$, $(R^3NCH_2CH_2)_t$, or $[(R^3R^4N^+CH_2CH_2)X^-]_t$; $R^3$ and $R^4$, independently, represent $C_1-C_{22}$ alkyl; X represents an anion; t is a positive integer; n and n', are each, independently, a positive number; and p is $\geq 0$, provide a skin substantive, occlusive moisture barrier covering for skin or hair. When $Y^1$ and $Y^2$ are O the polymers are nonionic in character when $Y^1$ or $Y^2$ represents $NR^3$ or $N^+R^3R^4X^-$ the polymers are cationic in character. The compositions have a moisturizing effect by reducing transepidermal water loss. The lipophilic or amphiphilic or hydrophilic film-forming polymers may be used individually or as mixtures as a delivery system for delivering pharmacological or cosmetic agents to the skin or hair.

18 Claims, 2 Drawing Sheets

CATIONIC FILM-FORMING POLYMER COMPOSITIONS, AND USE THEREOF IN TOPICAL AGENTS DELIVERY SYSTEM AND METHOD OF DELIVERING AGENTS TO THE SKIN

CROSS-REFERENCE TO RELATED APPLICATIONS

This application was filed as International Application PCT/US96/11001, filed Jun. 27, 1996, and designating the United States and also to U.S. application Ser. No. 08/496,413 filed Jun. 29, 1995 now abandoned. The disclosures of these applications are incorporated herein in their entirety, by reference thereto. This is a division of application Ser. No. 08/771,990, filed Dec. 23, 1996 now U.S. Pat. No. 5,807,957.

FIELD OF THE INVENTION

This invention relates to cationic film-forming polymer compositions which may be lipophilic, hydrophilic or amphiphilic and to the use thereof for topical application to the skin to modify the properties of the skin and/or to act as a reservoir for other agents. The invention also relates to the use of these cationic film-forming polymers alone or in combination with the non-ionic film-forming polymers of the aforementioned U.S. Ser. No. 08/496,413 now abandoned and PCT/US96/11001, and with therapeutic or cosmetic active agents for the topical and non-systemic delivery of these agents on and to the skin.

BACKGROUND OF THE INVENTION

The delivery of dermatological products to target cells within the layers of skin has been hampered by the variable rates of absorption and metabolism obtained by oral treatments and by absorption of the product into the blood stream or failure to be absorbed at all in transdermal drug delivery treatments. A large majority of dermatologic conditions have been traditionally treated by topical administration of drug and skin treatment agents. However, the skin's surface provides a natural barrier to these agents, often making effective topical delivery difficult. Topical administration is nevertheless often preferred to oral administration of drugs and other agents to treat dermatologic problems because substantially less drug enters the blood stream and systemic side effects can be eliminated or significantly reduced.

Various topical drug delivery systems are known in the art. These topical delivery systems generally fall into one of several major categories. A first category consists of traditional formulating agents such as, for example, ethanol, propylene glycol, various fatty compounds, and surfactants. Under certain conditions, these agents can function as penetration enhancers, but they generally do not provide prolonged duration of action of drugs or skin care agents. Frequently, they are not very effective unless used in doses that may cause skin irritation or other adverse side effects, or conversely may produce excessive and poorly controlled absorption, in particularly into the vascular system. A second category of skin care delivery systems are those that utilize specialized delivery technologies. These include, for example, liposomes, microspheres, transdermal patches and iontophoresis. Liposomes (a liquid encapsulation system) and microspheres (a solid entrapment system) require encapsulation of the drug or skin care agent, which may be complex, costly, or may introduce drug stability problems. Transdermal patches and iontophoresis can be used to treat dermatologic disorders, but these technologies may be impractical to use at multiple skin sites or on certain areas, such as the face. A third major category of known topical drug delivery systems includes non-invasive long-lasting liquid reservoirs for holding and depositing therapeutic or cosmetic agents in and on the stratum corneum and epidermis. An example of this type of topical delivery system are polyolprepolymers, which are hydroxy-terminated polyalkylene glycol-based polyurethane polymers that are capable of forming reservoirs in the upper layers of the skin, to hold and deposit therapeutic or cosmetic agents in an on the stratum corneum and epidermis. U.S. Pat. Nos. 4,971,800, 5,045,317 and 5,051,260, all to Chess, et al., relate to these compositions and methods. However, these polymeric agents tend to be viscous materials which are difficult to spread on the skin, and exhibit considerable drag, oily feel and tackiness.

In selecting a topical drug delivery system it is essential that adverse systemic effects and irreversible damage to the skin structure be avoided. It is also desirable that the compound itself not cause irritation or allergic response and that the delivery system is resistant to accidental removal and remains on and in the upper layers of the skin for an extended period of time. The delivery systems should also provide acceptable feel and spreadability. It is also desirable that the polymeric drug delivery system be compatible with a wide range of "active" agents and formulation ingredients.

BRIEF DESCRIPTION OF DRAWING FIGURES

FIGS. 3-A, 3-B and 3-C are schematic representations of untreated skin, skin treated with an amphiphilic hydrophilic) polymer according to the invention and skin treated sequentially with the hydrophilic polymer and then an occlusive hydrophobic (lipophilic) polymer according to the invention, respectively.

SUMMARY OF THE INVENTION

The present invention provides amphiphilic, hydrophilic or lipophilic urethane polymers of the type described in our aforementioned US and International applications but which are rendered cationic by incorporation into the polymer structure of certain tertiary amine or quaternary amine groups. Thus, in one aspect, the present invention provides compositions which are substantive to skin and hair and containing certain amphiphilic, hydrophilic or lipophilic urethane cationic polymer compounds, or mixtures thereof.

The terms "hydrophilic", "lipophilic", and "amphiphilic" refer to relative affinities for, and compatibility with, water versus typical oily/fatty organic materials. A simple test is to physically shake a sample of unknown material with a mixture of both water and a water immiscible organic solvent, such as octanol, until equilibrium is attained, and allow the liquid phases to separate. A substance found preponderantly in the water phase would be judged to be hydrophilic, while conversely a material going to the octanol phase would be considered lipophilic. Amphiphilic substances are those which show a substantial, although not necessarily equal, affinity for both; these will tend to concentrate at the interface of the two phases, characteristically resulting in a reduction in the interfacial tension.

The amphiphilic, hydrophilic and lipophilic compounds of this invention are film-forming cationic polymeric type compounds and have a generally linear, symmetrical structure with terminal hydrophobic hydrocarbon groups or polyalkylene oxide groups which, in one embodiment, are linked to the central urethanyl core groups via polyoxyalkyl amine groups or quaternized polyoxyalkyl amine groups; and, in an alternative embodiment polyoxyalkylamine groups or quaternized polyoxyalkylamine groups link together plural urethanyl groups. It is also part of the invention to provide the polymers with the tertiary amine or quaternary amine groups linking together the terminal groups to the central urethanyl core groups as well as linking together plural urethanyl groups.

As used herein the term "cationic" is intended to include the compounds with the polyoxyalkyl amine linking groups and which are cationic under acidic pH conditions as well as the quaternary group containing compounds.

These cationic compounds may be represented by the following formula (I):

$$R(CO)_m Y^1 - (CH_2CHR^1O)_n - [CONH - Z - NHCO(OCH_2CHR^2)_{n'} - Y^2 - (CH_2CH_2R^2O)_{n''}]_p - CONH - Z - NHCO - (OCH_2CHR^1)_n - Y^1(CO)_m R \qquad (I)$$

In the above formula (I) R represents (i) an alkyl, alkenyl, or alkaryl hydrocarbyl group of from 1 to 30 carbon atoms or (ii) a polypropylene oxide group (PPO) or polybutylene oxide group (PBO); $R^1$ and $R^2$, each, independently, represent a hydrogen atom, or a methyl or ethyl group; Z represents a divalent linking hydrocarbyl group; $Y^1$ represents O, $NR^3$ or $N^{\oplus}R^3R^4X^-$; $Y^2$ represents O, $NR^3$, $N^{\oplus}R^3R^4X^-$, $(R^3NCH_2CH_2)_t$ or $[(R^3R^4N^{\oplus}CH_2CH_2)X^-]_t$; $R^3$ and $R^4$ independently represent $C_1$–$C_{22}$ alkyl and X represents an anion; m is 0 or 1 with the provisos that $Y_1$ and $Y_2$ are not both oxygen (O) at the same time and that when $Y^1=NR^3$ or $N^{\oplus}R^3R^4X^-$, then m=0; n, n' and n", are each, independently, a positive number; p is $\geq 0$, preferably p is 0 or 1, and t is a positive integer. Most preferably, n, n', n" and p are selected such that 2n+pn'+pn" is at least about 20.

The groups R in formula (I) may be bonded to the polyalkyleneoxy group ($CH_2CHR^1O$) through either ether (m=0) or ester (m=1) linkages, when $Y_1$ is O. In general, ether linkages (m=0) are preferred because of their comparative chemical stability, especially where extremes in pH might be encountered. When $Y^1$ represents the amine group $NR^3$ or quaternary ammonium group $N^{\oplus}R^3R^4X^-$, then m=0. Preferably, $Y^1$ represents $NR^3$ or $N^{\oplus}R^3R^4X^-$.

The polymers of this invention are film-forming compounds which may be polar/hydrophilic, intermediate polarity/amphiphilic, or non-polar/lipophilic, depending primarily on the choices of R, $R^1$ and $R^2$. In general, larger R, $R^1$, and $R^2$ groups will tend to promote lipophilicity, while the smaller R, $R^1$, and $R^2$ groups will tend to increase hydrophilicity. Combinations of small and large groups among R, $R^1$ and $R^2$ will tend to produce amphiphilicity and consequent surface activity; since R, $R^1$ and $R^2$ can be controlled independently through choice of starting materials, various amphiphilic structures are possible, as will be obvious to those skilled in the art. Exemplary combinations are given in Table 1:

TABLE 1

| | R | $R^1$ | $R^2$ | Type |
|---|---|---|---|---|
| (i) | Short hydrocarbyl | H | H | Hydrophilic |
| (ii) | Short hydrocarbyl | H | Me, Et | Amphiphilic |

TABLE 1-continued

| | R | $R^1$ | $R^2$ | Type |
|---|---|---|---|---|
| (iii) | Long hydrocarbyl or PPO/PBO | H | H | Amphiphilic |
| (iv) | Long hydrocarbyl or PPO/PBO | Me, Et | Me, Et | Lipophilic |

In Table I "short hydrocarbyl" refers to approximately $C_1$–$C_4$ alkyl or alkenyl and "long hydrocarbyl" refers to an approximately $C_7$–$C_{30}$ alkyl, alkenyl or alkaryl. For intermediate carbon chain lengths the procedure described above can be used to determine whether any particular polymer is hydrophilic, amphiphilic or lipophilic.

In view of their relatively high molecular weights, (generally from about 1,000 to about 30,000) and the repeating polyoxyalkyl and diurethane units, these compounds may at times be referred to hereinafter as polymeric or polymer products. Especially within the more preferred molecular weight range of from about 1,000 to 25,000, more preferably, from about 2,000 to about 22,000, even more preferably, from about 2,000 to about 15,000 (i.e., wherein 2n+pn'+pn" ranges from about 20 to about 150), the polymers are substantive to skin, and provide occlusion and/or barrier properties, while themselves showing little or no actual penetration into the skin. Depending on the selection of, primarily, the polyoxyalkyl groups, (i.e., on $R^1$ and $R^2$), the polymers may exhibit one or more of the following properties: humectancy, wetting, emolliency, solubilization.

Similarly, the selection of the terminal hydrocarbyl group R will effect the properties of the polymer. For instance in the hydrophilic type (i) the preferred $C_1$–$C_4$ alkyl or $C_2$–$C_4$ alkenyl groups are only large enough to cap the hydroxyl groups provided by the polyoxyethylene group ($R^1=R^2=H$). Such compounds are considered truly hydrophilic. Conversely, longer alkyl, alkenyl, alicyclic, or alkaryl (R) terminal groups ensure that the polymer will, depending on $R^1$ and $R^2$, be amphiphilic and show surface activity ($R^1$ or $R^2=H$, type (iii)), or be essentially lipophilic ($R^1$ and $R^2=$Me or Et, type (iv)).

In general, the amphiphilic, hydrophilic or lipophilic character of the nonionic polymers of our aforementioned US and International applications retain the same "philic" character after incorporation of the tertiary amine or quaternary amine groups according to this invention. However, it is understood that the "philicity" may be modified to more or less hydrophilic, lipophilic or amphiphilic by the selection of the $R^3$ and $R^4$ groups. For example, polymers can be made more lipophilic by including as the $R^3$ and/or $R^4$ groups longer chain hydrocarbyl groups, especially having at least about 10 carbon atoms.

The selection of $Y^1$ and $Y^2$ will determine the ionic character of the polymer. When $Y^1$ and $Y^2$ are -O- then the polymer has a nonionic character. Such nonionic polymers are the subject matter of the aforementioned PCT/US96/11001 and U.S. Ser. No. 08/496,913, incorporated herein by reference. Conversely, when $Y^1$ and/or $Y^2$ represent one or more tertiary and/or quaternary amines at the polymer end groups or contained within the polymer backbone, respectively, the polymers have or may have a cationic character.

Specifically, the tertiary amine groups will be cationic to the extent that they are acid neutralized, whereas the quaternary amines will be cationic under all conditions. The amine and quaternary groups may be introduced through choice of starting materials; alternatively tertiary amine groups can be first incorporated into the polymer and quaternized later.

In the case of tertiary amine products, the dependency of degree of ionization on the extent of neutralization, i.e., on the pH, will in some cases provide an element by which cationic character can be separately controlled. Conversely, the amines can be used to neutralize acid components present in a formulation while simultaneously conferring the benefits of their polymeric structures. In addition these products can be used to produce quaternary derivatives that might otherwise not be practically attainable because, for example, of the unavailability of the requisite starting materials.

The urethane linkages used for coupling the polyoxyalkyl groups are stable and biocompatable and, may also contribute to physical properties. For example, in solution in appropriate solvents or carriers, the urethane groups may exhibit intermolecular hydrogen bonding and when applied topically, may provide specific bonding with skin proteins.

The bridging group Z (preferably alkylene or cycloalkylene of from 2 to about 16 carbon atoms) provides one or more sites of either relative rigidity or flexibility.

In general, the component groups of the invention polymeric compounds are derived from starting materials which are themselves widely accepted for use in the cosmetic, pharmaceutical and biomedical polymer areas.

In a particular aspect of the invention, mixtures of one or more generally hydrophilic and/or amphiphilic polymers and/or one or more generally lipophilic polymers in Table 1 are used in combination. Because of the general incompatibility of the hydrophilic or amphiphilic polymers and the lipophilic polymers, in the absence of a mutual solvent, such combinations will exist in phase separated form, although the common hydrophobic terminal groups will tend to preserve some association between these dissimilar polymers and so improve the gross uniformity of the mixture. The result is an intimate admixture wherein the hydrophilic and lipophilic phases function largely independently in terms of physical properties. For example, in a particular embodiment of this aspect of the invention, a hydrophilic depot matrix is formed beneath a water-resistant hydrophobic film via a single application of a solution of hydrophilic and lipophilic polymers in a volatile mutual solvent. By successive individual applications of different products, i.e., multipart systems, desired additive effects may be achieved.

The present invention also provides compositions for topical application to the skin or hair. These compositions include one or more of the polymeric urethanes of formula (I) described above and one or more active agents. The active agent or agents may be cosmetic, pharmaceutical or other biological or therapeutic substance. Because the polymers largely retain admixed formulation components, including active agents, while they themselves do not penetrate into or through the skin, such active agents tend to exhibit their cosmetic, pharmacological or other therapeutic or biological activity locally and non-systemically, i.e. do not enter into the bloodstream of the user.

In another particular aspect of the invention, the present invention provides a method for moisturizing skin or hair by topically applying to the skin or hair an occlusive moisture barrier effective layer of a lipophilic urethane polymer compound, such as the type (iv) in Table 1, above.

DETAILED DESCRIPTION OF THE INVENTION

The urethane film-forming polymeric compounds of this invention modify and improve upon the hydroxy-terminated urethane compounds of the formulas given in the aforementioned U.S. Pat. Nos. 4,971,800, 5,045,317, and 5,015,260 to Chess, et al., the disclosures of which are incorporated herein by reference thereto. Although the Chess, et al. patents describe the urethane compounds as penetration enhancers useful for topical or transdermal administration of pharmacologically active agent, subsequent work and studies by the Chess, et al. patentees and their assignee have shown that the urethane compounds are not effective as penetration enhancers for transdermal administration.

The urethane polymeric film-forming agents of this invention differ from the urethane compounds of, e.g., U.S. Pat. No. 4,971,800, primarily with respect to the replacement of the hydroxyl terminal groups with hydrophobic moieties R in the compounds of formula (I) through ester or ether linkages or through amine group linkages (amine or quaternary groups).

The hydrophilic, lipophilic and amphiphilic film forming cationic polymers of this invention may be represented by the following formula (I):

wherein R represents (i) a hydrocarbyl group, such as alkyl, alkenyl, or alkaryl, preferably alkyl or alkaryl group, of from 1 to 30 carbon atoms, or (ii) a polypropylene oxide group, $H(CH_3CH_2CH_2O)_r$ where r is a positive number of preferably from about 10 to about 60 or polybutylene oxide group $H(C_2H_5CH_2CH_2O)$ where s is a positive number of preferably from about 10 to about 60; $R^1$ and $R^2$, each, independently, represents a hydrogen atom, or a methyl (Me) or ethyl (Et) group; Z represents a divalent linking hydrocarbyl group; $Y^1$ represents O, $NR^3$ or $N^{\oplus}R^3R^4X^-$, $Y^2$ represents O, $NR^3$, $N^{\oplus}R^3R^4X^-$, $(R^3NCH_2CH_2)_t$ or $[(R^3R^4N^{\oplus}CH_2CH_2)X^-]_t$, $R^3$ and $R^4$, independently represent $C_1$–$C_{22}$ alkyl, and X represents an anion; m is 0 or 1, n, n' and n" are positive numbers; p is $\geq 0$, preferably 0 or 1; and t is a positive integer. $Y_1$ and $Y_2$ are not both oxygen atoms (O) at the same time. However, it is within the scope of the invention to include in combination with a cationic polymeric compound of formula (I) a nonionic polymeric compound having the same formula (I) but in which $Y_1$ and $Y_2$ are both oxygen atoms.

It is preferred, in order to achieve desirable molecular weights that when R represents the hydrocarbyl group (i), then n, n', n" and p are chosen such that the total number of alkylene oxide groups in the molecule, 2n+pn'+pn", is at least about 20, such as from about 20 to about 400. Similarly, when R represents the propylene oxide group (PPO) or butylene oxide group (BPO) (ii), then 2n+pn'+pn"+r or 2n+pn'+pn"+s, respectively, is at least about 20, such as from about 20 to about 400.

The amine group containing cationic-type film-forming polymers of this invention may be represented by the following formula (I)-1 or (I)-2:

where R, $R^1$, $R^2$, Z, n, n', n" and p are as defined in formula (I),

$Y^a$ represents O, COO, $NR^3$ or $N^{\oplus}R^3R^4X^-$, and
$Y^b$ represents $NR^3$, $N^{\oplus}R^3R^4X^-$, $(R^3NCH_2CH_2)_t$ or $[(R^3R^4N^{\oplus}CH_2CH_2)X^-]_t$,
where $R^3$, $R^4$ and t are as defined in formula (I);

where R, $R^1$, $R^2$, Z, n, n' and p are as defined in formula (I) and

$Y^c$ represents $NR^3$ or $N^{\oplus}R^3R^4X^-$ where $R^3$, $R^4$ and $X^-$ are as defined above.

The lipophilic film forming polymer of formula (I) may be represented by the general formula (I-a):

$$R^a(CO)_mY^1-(CH_2CHR^{11}O)_n-[CONH-Z-NHCO(OCH_2CHR^{12})_{n'}-Y^2-(CH_2CHR^{12}O)_{n''}]_p-CONH-Z-NHCO-(OCH_2CHR^{11})_n-Y^1(CO)_mR^a \quad (I\text{-}a)$$

where $Y^1$, $Y^2$, Z, m, n, n', n" and p are as defined in formula (I), $R^a$ represents a $C_1$-$C_{30}$ hydrocarbyl group, such as alkyl, alkenyl or alkaryl, preferably alkyl or alkaryl, $R^{11}$ and $R^{12}$ represent methyl or ethyl groups. $R^a$ preferably represents $C_5$-$C_{30}$ alkyl, especially $C_8$-$C_{26}$ alkyl, or $C_7$-$C_{30}$ alkaryl. $R^3$ and/or $R^4$ also are preferably long chain alkyl groups, e.g., at least about 10 carbon atoms, such as from 10 to 22 carbon atoms to further increase the lipophilic character, namely, solubility in lipophilic solvents.

The hydrophilic film-forming polymer of formula (I) may be presented by the general formula (I-b1):

$$R^b(CO)_m-Y^1(CH_2CH_2O)_n-[OCNH-Z-NHCO(OCH_2CH_2)_{n'}-Y^2-(CH_2CH_2O)_{n''}]_p-CONH-Z-NHCO-(OCH_2CH_2)_n-Y^1(CO)_mR^b \quad (I\text{-}b1)$$

where $Y^1$, $Y^2$, Z, m, n, n', n" and p have the same meanings as in formula (I); and $R^b$ represents a short hydrocarbyl group, such as $C_1$-$C_6$ alkyl or $C_2$-$C_6$ alkenyl, preferably, $C_1$-$C_4$ alkyl.

The amphiphilic film-forming polymer of formula (I) may be represented by the general formula (I-b2):

$$R^c(CO)_mY^1-(CH_2CHR^1O)_n-[CONH-Z-NHCO(OCH_2CHR^2)_{n'}Y^2-(CH_2CHR^2O)_{n''}]_p-CONH-Z-NHCO-(OCH_2CHR^1)_n-Y^1(CO)_mR^c \quad (I\text{-}b2)$$

where $Y^1$, $Y^2$, Z, $R^1$, $R^2$, m, n, n' and p have the same meanings as in formula (I); and $R^c$ represents a short hydrocarbyl group, such as alkyl or alkenyl having from 1 to about 6 carbon atoms, preferably $C_1$-$C_4$ alkyl, or a long hydrocarbyl group having from about 7 to about 30 carbon atoms, such as $C_7$-$C_{30}$, preferably $C_7$-$C_{28}$, more preferably $C_8$-$C_{26}$, and especially preferably $C_{12}$-$C_{22}$, alkyl, alkenyl or alkaryl group; with the proviso that when $R^c$ represents a short hydrocarbyl group one of $R^1$ or $R^2$ (p≠0) is a hydrogen atom and the other is methyl group or ethyl group; and when $R^c$ represents a long hydrocarbyl group then $R^1$ and $R^2$ both represent hydrogen atoms.

In the above formulas (I-a), (I-b1) and (I-b2), 2n+p(n'+n") is preferably at least about 20, such as from about 20 to about 400.

The nonionic film-forming polymers of formula (I) which may be included in the compositions of this invention may be represented by the following formula (I)-3:

$$R-(CO)_mO-(CH_2CHR^1O)_n-[CONH-Z-NHCO-(OCH_2CHR^2)_{n'}]_p-CONH-Z-NHCO-(OCH_2CHR^1)_n-O(CO)_mR \quad (I)\text{-}3$$

where R, $R^1$, $R^2$, Z, m, n, n' and p are as defined in formula (I).

In addition to the preferred hydrocarbyl groups represented by $R^a$, $R^b$ and $R^c$ in formulas (I-a), (I-b1) and (I-b2), respectively, $R^a$, $R^b$ and $R^c$ may also represent propylene oxide groups, $H(CH_3CH_2CH_2O)_r$, or butylene oxide groups, $H(C_2H_5CH_2CH_2O)_s$ where the value of r or s, representing the number of propylene oxide groups or butylene oxide groups, respectively, is selected to provide the desired hydrophilic, amphiphilic, or lipophilic property.

Furthermore, in the above and following formulas it will be appreciated that references to molecular weights refer to weight average molecular weights and, similarly, the number of the repeating alkylene oxide units represented by n, n', n", p, q, r and s, will typically be average values. Similarly, depending on the source of the hydrocarbyl group for R, such as in the hydrocarbon-terminated glycols of formula (II) as described below, it will be understood by those skilled in the art that mixtures of, e.g., alkyl groups or alkenyl groups, of different carbon chain lengths may be present.

The nonionic polymers of formula (I)-1, including nonionic polymers corresponding to the above formulas (I-a), (I-b1) and (I-b2), where $Y_1$ and $Y_2$ are both oxygen atoms, may be prepared by reacting hydrocarbon-terminated linear alkyl, alkenyl or alkaryl glycols with a monomeric organic diisocyanate to form the hydrocarbon-terminated urethane compounds of this invention, as described in more detail in the aforementioned applications U.S. Ser. No. 08/496,413 and PCT/US96/11001.

The amine/cationic polymers of formula (I) and, particularly formula (I)-1 and (I)-2 may be prepared similarly by reacting hydrocarbon terminated linear alkyl, alkenyl or alkaryl tertiary amines or quaternary ammonium compounds with the aforementioned monomeric organic diisocyanate to form the subject polymers. Alternatively, the quaternized amine compounds may be obtained by incorporating the tertiary amine compounds in the polymer and then quaternizing by any of the well known and conventional methods, for example, direct alkylation with quaternizing reagents, such as, ethyl chloride, dimethyl sulfate, and the like.

In the case of the ethylated amine and ethylated quaternary amine groups for $Y^2$, derivatives of commercially available polyethyleneimines, (e.g., the Epomins from Nippon Shokubai Co.) are used as starting materials. Alkylation to form the tertiary amine or quaternary amine can be prepared as described. Reaction with 2 moles of ethylene oxide would result in the appropriate hydroxyl terminated raw material.

The inclusion of the amine groups, and especially cationic amine groups, will generally increase the polarity of the molecule beyond that already provided by existing structural units, which in turn will tend to promote, e.g., water solubility and increase hydrophilic-lipophilic balance relative to nonionic analogs.

In addition, amines will produce specific binding and therefore substantivity to anionic structures, in particular to surfaces such as skin and hair. Furthermore cationics normally tend to neutralize adventitious negative charges and thus the polymers can provide antistatic coatings. In consequence, improved durability on skin or hair and/or antistatic properties of polymers simultaneously functioning as humectants, emollients, etc., will be obtained in many cases. The cationic polymers may also have antimicrobial properties, especially where $Y^1$ and/or $Y^2$ are quaternary ammonium groups.

Suitable representative hydrocarbon-terminated tertiary amine compounds useful as intermediates may be represented by the general formula (VI):

$$R^3-\underset{\underset{R}{|}}{N}-(OCH_2CHR^1)_nOH \quad (VI)$$

wherein R, $R^1$, $R^3$ and n are defined above.

Representative examples of the hydrocarbyl group R include alkyl of from 1 to 30 carbon atoms. The alkyl may be linear, branched or cyclic. In the case of hydrophilic polymers lower alkyl of from 1 to 6 carbon atoms, especially from 1 to 4 carbon atoms are preferred. Examples include methyl, ethyl, n-propyl, i-propyl, n-butyl, i-butyl, t-butyl. Examples of cycloalkyl groups include cyclopropyl, cyclobutyl, cyclopentyl, and cyclohexyl. The cycloalkyl groups may also include lower alkyl group substituents generally of from 1 to 2 carbon atoms, such as methylcyclopropyl, ethylcyclobutyl, etc. For amphiphilic and lipophilic polymers hydrocarbyl group R will preferably have from about 7 to 28 carbon atoms, especially preferably from about 12 to 22 carbon atoms, such as, for example, heptyl, octyl, nonyl, dodecyl, octadecyl, eicosyl, heptenyl, octenyl, decenyl, myristyl, hexadecenyl, etc. Examples of alkylaryl groups include benzyl, tolyl, phenethyl, trimethylphenyl, hexylphenyl, nonylphenyl, dodecylphenyl, and the like. Similarly, when R represents alkenyl, the alkenyl may be linear or branched or cyclic. R may also represent a polypropylene oxide group, i.e., H$(CH_3CH_2CH_2O)_r$, where r is a positive number of from about 10 to about 60, preferably from about 15 to 50; or polybutylene oxide group, i.e., H$(C_2H_5CH_2CH_2O)_s$, where s is a positive number of from about 10 to about 60, preferably from about 15 to about 50. Polypropylene oxide is the preferred polyalkylene oxide group.

Representative examples of the alkyl groups for $R^3$ include, for instance, methyl, ethyl, propyl, isopropyl, n-, i-, sec-, and tert-butyl, n-pentyl, n-hexyl, 4-methyl-1-pentyl, 4-ethyl-1-pentyl, 3-methyl-1-pentyl, n-octyl, n-nonyl, n-decyl, dodecyl, octadecyl, eicosyl and the like.

Suitable representative hydrocarbon-terminated quaternary ammonium compounds may be represented by the following general formula (VII):

(VII)

wherein R, $R^1$, $R^3$, $R^4$, and n are as defined above. Representative examples of R and $R^3$ are as mentioned above. Representative examples of $R^4$ are the same as mentioned above for $R^3$.

Representative examples of the anion X include, for instance, $Cl^-$, $Br^-$, $SO_4^=$, $HSO_3^-$, $CH_3SO_4^-$ and the like.

Similarly to the preparation of the nonionic polymers, in the case of the amine/cationic polymers of formula (I)-1 and (I)-2, glycols represented by the following general formula (III) may also be included as intermediate:

(III)

wherein $R^2$ and n' are as defined above. n' represents a positive number and generally may be up to about 400, preferably at least 2, such as from about 4 to about 200, more preferably from about 10 to about 180, especially preferably from about 20 to about 150.

When $R^2$ represents hydrogen, the compounds of formula (III) are polyethylene glycol derivatives; when $R^2$ represents methyl, they are polypropylene glycol derivatives; and when $R^2$ represents ethyl, formula (III) represents polybutylene glycol derivatives.

Where glycols of formula (III) are included, they may be reacted with the organic diisocyanate in admixture with the hydrocarbon-terminated glycols of formula (II) or in a sequential manner, as will be obvious to those skilled in the art of polyurethane synthesis.

Mixtures of various reactive polyalkylene glycols or polyalkaryl glycols can be employed in preparing the hydrocarbon-terminated urethane film forming polymer compounds used in the practice of the present invention. Moreover, in the case of formula (I)-2 when p≠0 a diglycol of the following general formula (III-A) will be included as an intermediary (III-A)

where $R^2$, $Y^b$, n' and n" are as defined above.

In formulating the hydrocarbon-terminated urethane compounds of this invention, a wide variety of monomeric organic diisocyanates can be used. These diisocyanates are represented by the general formula wherein Z is a divalent hydrocarbyl linking group, such as alkylene, or alkenylene, arylene or alkylarylene radical, generally one containing from about one to about 20 carbon atoms. The alkylene or alkenylene radical may be straight or branched or cyclic (from about 5 to about 10 carbon atoms) such as, for example, dimethylene, trimethylene, dimethyltrimethylene, cyclopentylene, cyclohexylene, cyclohexenylene, propenylene, butenylene, hexamethylene, octenylene, decamethylene and the like. In the case that Z is an alkenylene radical, it is generally one having between one and about three double bonds, preferably one double bond. When Z represents aryl it may be a mononuclear or fused ring arylene radical, generally one containing from about six to about ten carbon atoms, such as phenylene or naphthalene, all of which can be substituted, e.g. with alkyl groups, generally alkyl groups having up to six carbon atoms, aryl groups, which may be substituted with amine moieties, nitro, lower (1–6C) alkyl, lower (1–6C) alkoxy, lower (1–6C) alkoxy-substituted lower (1–6C) alkyl, halogen, and the like. Included among such diisocyanates mention may be made, for example, of aromatic diisocyanates, such as, m-phenylenediisocyanate, p-phenylenediisocyanate, 4-t-butyl-m-phenylenediisocyanate, 4-methoxy-m-phenylenediisocyanate, 4-phenoxy-m-phenylenediisocyanate, 4-chloro-m-phenylenediisocyanate, toluenediisocyanates (either as a mixture of isomers, e.g., the commercially available mixture of 80% 2,4-toluenediisocyanate and 20% 2,6-toluene-diisocyanate, or as the individual isomers themselves), m-xylylenediisocyanate, p-xylylenediisocyanate, cumene-2, 4-diisocyanate, durenediisocyanate, 1,4-naphthylenediisocyanate, 1,5-naphthylenediisocyanate, 1,8-naphthylenediisocyanate, 2,6-naphthylenediisocyanate, 1,5-tetrahydronaphthylene-diisocyanate, p,p-diphenyldiisocyanate, diphenylmethane-4,4'-diisocyanate, 2,4-diphenylhexane-1,6-diisocyanate, bitolylenediisocyanate (3,3'-dimethyl-4,4'-biphenylene-diisocyanate), dianisidinediisocyanate (3,3'-dimethoxy-4,4'-biphenylenediisocyanate), aliphatic diisocyanates, such as methylenediisocyanates, ethylenediisocyanate, the tri-, tetra-, penta-, hexa-, octa-, nona- and decamethylene-,α-ω-diisocyanates, isophorone diisocyanate, bis(4-isocyanatocyclohexyl)methane, 2-chloro-trimethylene-diisocyanate, 2,3-dimethyl-tetramethylenediisocyanate, and the like, as well as mixtures thereof.

By virtue of the hydrophobic terminal groups, the urethane polymers are rendered amphiphilic when $R^1$ or $R^2$ is H and can be more readily tailored for specific end use applications and product types which were not available for the hydroxyl terminated urethane compounds described in the aforementioned patents to Chess.

Similarly, the selection of $R^3$ and $R^4$ will have an effect on the "philicity" of the resulting polymer and polymer mixtures. This effect will generally be similar to the effect on "philicity" of the group R (when R is the hydrocarbyl group). That is, as the group $R^3$ or $R^4$ becomes larger the polymer becomes more lipophilic, all other variables remaining constant. The net effect on hydrophilicity, or lipophilicity, will depend on the other structural units, primarily R, $R^1$ and $R_2$.

Moreover, since ionic groups are invariably hydrophilic, the cationic polymers tend toward hydrophilic or amphiphilic, but not completely lipophilic. However, for large $R^3$ and/or $R^4$, e.g., 10 or 12 or 14 or more carbon atoms, the polymer tends to become more lipophilic.

Figure 1:
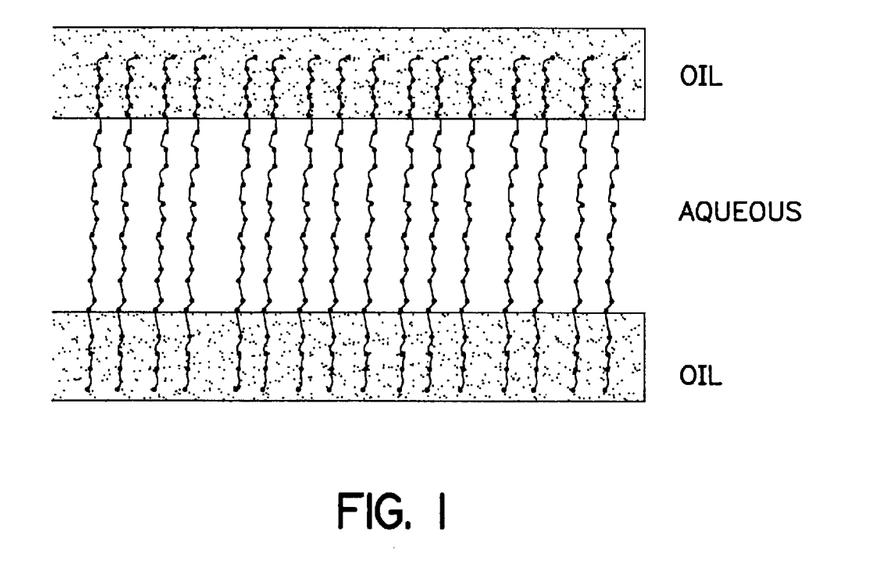
FIG. 1 is a schematic view representing a bilayer liposome structure which may be formed by the polymers of this invention.

In the amphiphilic type products, the hydrophobe terminated polymers of this invention form molecular bilayer structures, such as liposomes. Thus, as shown schematically in FIG. 1, the α, ω-terminal hydrophobe R groups are compatible with and bind the opposed oily layers (10) while the interior hydrophilic polyoxyalkyl moieties and urethane groups bind to an intermediate aqueous phase (20).

Figure 2:
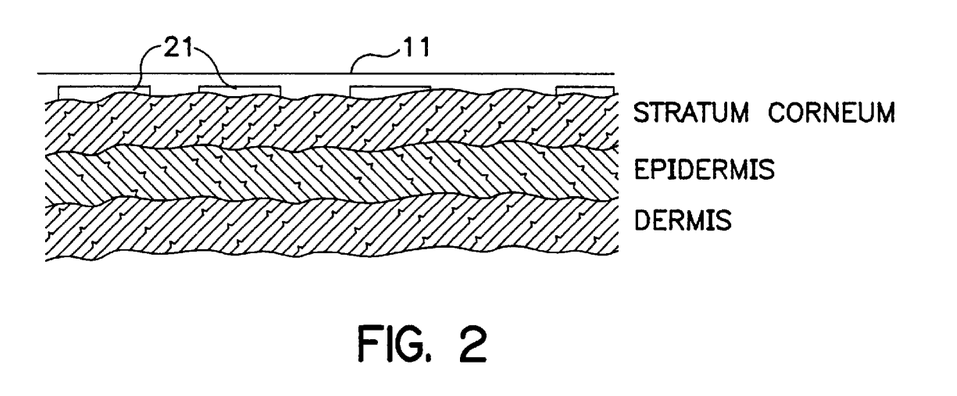
FIG. 2 is a schematic view, in elevation, representing a two layer polymer system according to the invention as applied to skin.

The hydrophobe terminated urethane film-forming polymers of this invention may also be used to form a multilaminar depot system by mixing hydrophilic/amphiphilic and lipophilic products. The respective polymers will tend to undergo phase separation due to their partial incompatibilities while maintaining an intimate association between the discrete phases due to the chemical similarities in the structure. By proper selection of the R, $R^1$ and $R^2$ groups and the values of n and n' (when p≠0), a structure such as shown in FIG. 2 may be obtained. In FIG. 2, discrete hydrophilic phases 21 are held in intimate contact with the stratum corneum skin layer SC beneath a continuous or substantially continuous film layer of water resistant hydrophobic phase 11. Hydrophilic phases 21 can, therefore, readily function as a depot matrix for any water soluble or water dispersible active agent present in the hydrophilic phase. Depending on the nature of the active agent it may penetrate into the stratum corneum layer SC and, perhaps, through the stratum corneum into the epidermis E or dermis D.

When mixtures of hydrophilic/amphiphilic polymer and lipophilic polymer are used the amounts of each may vary widely, depending on such factors as desired properties, the degree of "philicity" or "phobicity," other additives and/or actives, etc. Generally, however, based on 100 parts by weight of the mixture, from 0.5 to 95 parts by weight of each type of polymer may be present. Moreover, based on the total composition, amounts of each type of polymer may generally be within the range of from about 0.5 to 25 wt %, preferably, from about 1 to 10 wt %. More broadly, however, compositions for topical or dermal administration can contain, for example, from about 0.5 wt %, preferably from about 1 wt %, and up to about 99 wt % of compound, or mixture of compounds of formula (I).

The mixture of amphiphilic or hydrophilic polymer and lipophilic polymer may be deposited on the skin by any of the usual methods known to the art of formulating topical compositions. In particular, it is preferred to cast the polymer mixture dissolved in a mutual volatile solvent (e.g. ethanol, ethylacetate, and the like). When the resulting solution is applied to the skin, the volatile solvent will evaporate leaving behind a film residue of the polymer mixture and any other components which may have been incorporated into the composition. During the drying phase, the respective polymers will phase separate in accordance with their intrinsic incompatibility. As shown in FIG. 2 the more hydrophilic polymer will tend to form discrete hydrophilic portions 21 adherent to the stratum corneum. A continuous layer 11 of the more lipophilic polymer can overlie and form an occlusive protective barrier for the hydrophilic polymer phase and any water soluble or hydrophilic active agents present in the hydrophilic polymer phase. Generally, other additives will be distributed in the lipophilic polymer and/or hydrophilic and/or amphiphilic polymer depending on their respective affinities for the polymers.

The polymer mixture may be dissolved in any volatile solvent in which both polymers are soluble and which is generally recognized as safe for topical application to the skin. In addition to ethanol and ethyl acetate, the volatile solvent may be aqueous or non-aqueous. The selection of the volatile solvent can be easily made by the practitioner depending on, for example, the solubilities of each respective polymer as well as any other component(s) which may be included in the composition.

Moreover, while the two layer structure shown in FIG. 2 may be obtained by the single application of a mixture of hydrophilic (or amphiphilic) and lipophilic polymers, the invention also contemplates successive applications of different types of polymer(s) and active agent(s) to achieve different additive effects and multilaminar structure.

The film-forming polymers of this invention may be used by themselves or in combination with one or more active agents. As used herein the term "active agent" is intended to include, not only cosmetic, pharmacological, or other therapeutic or biological activity, but also skin penetration enhancers, such as, fatty alcohols, fatty esters, alkyl-1,3-dioxolanes, etc. Skin penetration enhancers are not themselves intended to exert a physiological effect. Rather, they enable or facilitate penetration of other active agents present in the formulation. Therefore, control of the availability of the skin penetration enhancers to the skin, as made possible by this invention, will have the practical effect of regulating the penetration of the cosmetically or pharmacologically active agents.

When used alone, the lipophilic polymer will generally be formulated as a hydrophobic (occlusive) film-forming polymer that is substantive to skin, hair or other epithelial tissue. Applying a thin layer of such polymer to the skin, hair, etc. will serve to retain moisture present in or added to the skin by reducing transepidermal water loss (TEWL). Because of its high substantivity to skin the dermal water retention (TEWL reduction) effects may be long lasting.

Even longer lasting and more effective moisture retention and skin softening effects may be achieved by successive applications of a layer of non-occlusive, hydrophilic urethane polymer followed by a layer of an occlusive hydrophobic or lipophilic urethane polymer. Furthermore, either or both (or neither) of the non-occlusive and occlusive film layers may include moisturizers or active agent(s) with or without penetration enhancers.

Figure 3A:
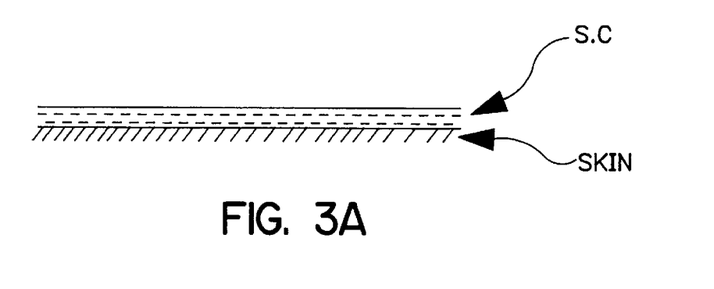
Figure 3B:
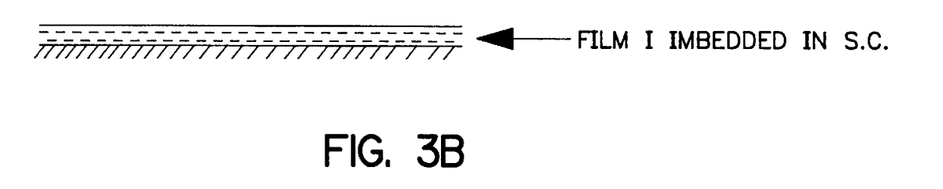
Figure 3C:
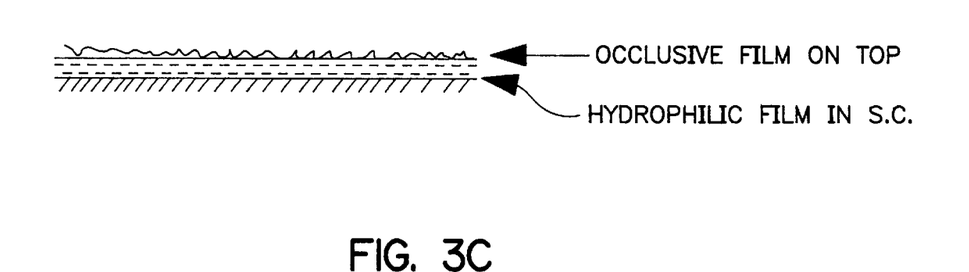

The application of such double film system is schematically illustrated in FIGS. 3A–3C. FIG. 3-A is a schematic representation of untreated skin including the stratum corneum outer layer SC and the epidermal and dermal sublayers E/D. As shown in FIG. 3-B, hydrophilic polymer (usually applied in the form of solution or gel as described below) is first spread over a defined area of the skin. The hydrophilic polymer partially penetrates into the stratum corneum (SC) upper skin layer to form a first film 22 embedded in the SC layer. The film 22 concentrates moisture from the skin on top of or in the SC layer. Next, as shown in FIG. 3-C, a solution or gel formulation of hydrophobic/lipophilic polymer is applied over the previously treated area of the skin to form an occlusive film layer 12. The viscosity of the hydrophobic polymer formulation, coupled with its general incompatibility with the first polymer film 22 results in a substantially uniform occlusive film layer 12 which overlies the SC layer and serves, with the layer 22, to maintain a high moisture concentration in the SC layer.

The formation of a hydrophobic (occlusive) film layer can be readily demonstrated by addition of a drop of water, which will characteristically bead up on the surface of film layer 12. This beading up is a manifestation of a high contact angle (θ), that is, one approaching 90° between the edge of the droplet and the surface. The exact value of θ and the corresponding degree of hydrophobicity can be measured using methods well known in the art of surface measurement. The resulting reduction in TEWL can also be measured using techniques well known in the art of skin characterization.

Methods of synthesizing urethanes are well known in the art. U.S. Pat. No. 2,266,777, for example, issued in 1941, describes the reaction of isocyanate compounds with polyhydroxy alcohols to form polyurethanes, now a standard synthetic method. Reference may also be made to Saunders, *Polyurethane: Chemistry and Technology* (New York: Wiley & Sons, 1961) for an overview of the chemistry of urethanes.

In preparing the urethane polymeric compounds of this invention, the mole ratio of diol to diisocyanate is about 1:1, and the reaction is carried out at an elevated temperature (at least about 100° F., and preferably at least about 150° F.; temperatures may be higher depending on the particular reactants and on the amount of catalyst used) with constant mixing. The solvent, if used, is a suitable organic solvent, such as, dioxane, xylene, cyclohexane or the like. The use of catalysts is optional. Suitable catalysts include organic tin alkyl titanates or octoates and amines such as those in the Dabco group (i.e., Dabco DC-1, DC-2, R-8020, R-595, 33 LV, DF and WT, all available from Air Products and Chemicals, Inc., Allentown, Pa., under the "Dabco" trademark) and N-ethyl morpholine. Further information regarding analogous reactions may be found in U.S. Pat. Nos. 2,266,777 and 2,282,827, the disclosures of which are hereby incorporated by reference in their entirety.

The preferred values for p in the polymers of the present invention are 0 or 1, although it is recognized that as a natural consequence of their synthesis some amount of higher polymer may result. The value p for the compounds of Formula I may increase above 1 during synthesis by varying the reaction temperature, or the amount, if any, of water in the reaction mixture; for example, increasing the water content will typically result in a more highly polymerized structure, i.e. one having a higher p value. Selection of reaction conditions herein is believed to be well within the skill of the art, and may in any case be readily derived from the aforementioned references on urethane chemistry.

The polymers of formula (I) can be used alone or in compositions for topical administration of a dermatological agent or cosmetic agent. Pharmacological or biological active agents may also be administered or applied to the skin with the polymers of this invention. The compositions deposit and hold drugs and skin care agents at targeted levels on and in the upper layers of the skin, rather than for delivering the drugs or agents into the blood stream.

The invention compositions include a mixture of two or more film forming urethane polymers of formula (I) including at least one hydrophilic/amphiphilic polymer and at least one lipophilic polymer, as previously described.

However, in accordance with another aspect of the invention there are also provided compositions which include a mixture of a hydrophilic/amphiphilic polymer of formula (I) with lipophilic polymer of the formula (IV)

$$R(CO)_mO-(CH_2CHR^{12}O)_q(CO)_mR \qquad (IV)$$

where m, R and $R^{12}$ are as previously defined and q is a positive number of at least 2 and up to about 400, such as from about 2 to 200.

In still another alternative embodiment, the present invention provides compositions based on a mixture of a lipophilic polymer of formula (I-a) with a hydrophilic polymer of formula (V):

$$RO-(CH_2CH_2O)_qR \qquad (V)$$

and where R and q are as previously defined. In any specific combination of polymers, the average values of m, n, n', n'', p, q, r, s, R, $R^1$, $R^2$, $R^{11}$, and $R^{12}$ do not have to be the same for each polymer of the mixture.

Compositions containing the mixture of a polymer of formula (I), e.g., (I-a), (I-b1), (I-b2), with a polymer of formula (IV) or formula (V) may be prepared and used in the same manner as previously described for the compositions based on mixtures of polymer(s) of formula (I).

The film-forming polymer(s) may be dispersed within a suitable topical carrier. A selected "active" agent, which may be, for example, pharmacologically active agent, dermatological agent, cosmetic agent, humectant, or other skin care or treating agent may also be present in the composition. The topically applied compositions are effective for enhancing adherence of active agent on and to the skin as well as for retaining moisture.

By "topical administration" or "dermal administration" is meant the local, non-systemic administration of a topical pharmacologically active agent or cosmetic agent on the skin, that is, without passage of the agent into the blood stream.

"Topical carriers" as used herein refer to vehicles suitable for topical applications of drugs or cosmetics, and include any such liquid or non-liquid solvent, diluent or the like materials known in the cosmetic and medical arts, for forming any liquid or semisolid gel, cream, ointment, emulsion, aerosol, foam, lotion, or the like, and which does not adversely affect living animal tissue or interact with other components of the composition in a deleterious manner. Topical carriers are used to provide the compositions of the invention in their preferred liquid form. Examples of suitable topical carriers for use herein include water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials, and mixtures thereof.

By the terms "pharmacologically active agent" or "drug" as used herein is meant any chemical material or compound suitable for topical administration which induces any desired local effect. Such substances include, for example, antifungal agents, chemotherapeutic agents, antibiotics, antimicrobial agents, antiviral agents, hormones, cutaneous growth enhancers, including for the hair and nails, hair care agents, antipsoriatics, retinoids, anti-acne medicaments, antineoplastic agents, topical anesthesetics, phototherapeutic agents, sunscreens, cutaneous protection agents, alpha-hydroxy acids (including lactic acid and glycolic acid), insect repellants and the like.

Locally administered topical cosmetic agents include, for example, hair or skin care agents, including colorants and mascaras, moisturizers, skin or hair softeners, pigment modulators, antiproliferatives, antipsoriatics, retinoids, anti-acne medicaments, antineoplastic agents, phototherapeutic agents, sunscreens, cutaneous protection agents, alpha-hydroxy acids including lactic and glycolic acids, and the like.

By "effective" amount of a pharmacologically active agent is meant a nontoxic but sufficient amount of a compound to provide the desired local effect and performance at a reasonable benefit/risk ratio attending any medical treatment. An "effective" amount of a skin permeation enhancer as used herein means an amount selected so as to provide the desired increase in permeability of the upper layers of skin and, correspondingly, the desired depth of penetration, rate of administration, and amount of drug delivered.

The hydrophobic-group terminated urethanes of this invention may be used to pretreat skin or other epithelial tissue prior to topical administration of pharmaceutical or cosmetic agent. Alternatively, and preferably, the hydrophobic-terminated urethane is administered concurrently with the pharmaceutical or cosmetic agent. The hydrophobic-terminated urethane may be administered with or without a topical carrier, but preferably with a topical carrier. A formulation may include as little as about 0.5 wt %, such as from about 1–99 wt. % hydrophobic-terminated urethane compound or compounds of formula (I), preferably from about 3–95 wt. % hydrophobic-terminated urethane compound(s). Most preferably, the present formulations contain from 10 to 50 wt % of the hydrocarbon-terminated urethane compound or compounds of formula (I).

Exemplary carriers that may be used herein include water, alcohols, including both monohydric and polyhydric alcohols, e.g. ethanol, isopropanol, glycerol, sorbitol, 2-methoxyethanol, diethylene glycol, ethylene glycol, hexylene glycol, mannitol and propylene glycol; ethers such as diethyl or dipropyl ether; polyethylene glycols and methoxypolyoxyethylene; carbowaxes having molecular weights ranging from 200 to 20,000; polyoxyethylene glycerols; polyoxyethylene; sorbitols; and stearoyl diacetin.

The topical carriers described herein include various agents and ingredients commonly employed in dermatological and cosmetic ointments, creams, gels, aerosols, foams and lotions. For example, one or more of excipients, fragrances, opacifiers, preservatives, anti-oxidants, gelling agents, perfumes, thickening agents such as carboxymethylcellulose, stabilizers, surfactants, emulsifiers, emollients, color agents, aerosol propellants, foaming agents, and the like may be present.

The amount of pharmacologically active agent will depend on a variety of factors, including the disease to be treated, the nature and activity of the agent, the desired effect, possible adverse reactions, the ability and speed of the agent selected to reach its intended target, the cost and availability of the agent, the use of two or more pharmacologically active agents, and other factors within the particular knowledge of the patient and physician.

As noted above, the compositions of the present invention may be used with any number of pharmacologically active agents which may be topically administered. Examples of pharmacologically active agents suitable for use in conjunction with the present invention include urea and lactic acid, e.g., in treating X-linked ichthyosis, a genetic skin disease characterized by excessive scaling.

The compositions of the present invention are similarly useful in facilitating the adherence of locally administered topical medicaments such as cosmetics, sunscreens, insect repellents or the like, and as skin emollients and moisturizing agents.

Any particular formulation will further depend on the chemical nature of the pharmacologically active agent to be administered as well as on the depth of cutaneous penetration desired. The method of delivery may also vary, but necessarily involves applying the formulation of the present invention to skin or hair or other epithelial tissue for a period of time sufficient to allow the desired penetration of the selected drug or topical medicament. The method may involve direct application of the inventive composition as an ointment, gel, cream or the like.

The hydrocarbon-terminated polymers and drug(s) and/or cosmetic(s) may be separately added to a base carrier formulation. Alternatively, the pharmacological drug or polymers cosmetic compound may be added to the polymer or polymers and the mixture blended with the base carrier.

The hydrocarbon-terminated urethane compounds of this invention may be used without other active ingredient as skin moisturizing agents. The invention thus includes a method of moisturizing skin using these compounds. The invention polymers may also be used in a method of treating proliferative skin diseases. These conditions are typically characterized by epidermal cell proliferation or incomplete cell differentiation, and include, for example, X-linked ichthyosis, psoriasis, atopic dermatitis, allergic contact dermatitis. Also included are ailments such as mange that are specific to nonhuman animals. A preferred formulation for use as a moisturizing agent includes from at least about 0.5 wt % and up to about 25 wt. % hydrocarbon-terminated urethane, preferably from 1 to 10% by weight, in a topical carrier as described above. Such a formulation causes a lipophilic "barrier" to form at the skin surface, causing retention of moisture thereon.

For example, the hydrophilic and hydrophobic polymers of this invention can be formulated into separate compositions for use as a dual film topical drug delivery system or skin moisturizing system. Such a drug delivery system includes a first composition (A) containing a film forming hydrophilic polymer and a second composition (B) containing a film forming hydrophobic polymer, the latter composition being incompatible with the hydrophilic composition. Each composition is formulated as a cream, solution, or gel, for example, to enable application of the first composition directly on the skin and application of the second composition over the first composition.

The hydrophilic film forming polymer of the first composition (A) is a humectant-type of polymer, formed, for example, by reacting a polyethylene glycol derivative with diisocyanate. The first composition (A) may optionally contain a penetration enhancer, a co-enhancer, a pharmacologically active agent, or a combination thereof.

The amounts of each of the hydrophilic polymer and hydrophobic/lipophilic polymer may vary widely depending on the nature and use of the composition and the individual polymers and other additives. Generally, however, the compositions may contain from about 0.5 to 99.5 parts by weight of hydrophilic polymer and from about 0.5 to 99.5 parts by weight of hydrophobic polymer based on the total amount of these polymers.

The second composition (B) contains an occlusive hydrophobic film forming polymer and may optionally contain a penetration enhancer, co-enhancer, pharmacologically active agent, or a combination thereof.

The dual film topical delivery system of this invention thus contains a film forming humectant hydrophilic polymer composition and a film forming occlusive hydrophobic polymer composition, each or either of which may optionally contain a pharmacologically or cosmetically active agent, penetration enhancer, co-enhancer, or combinations thereof.

Use of the dual film topical drug delivery system of this invention is schematically shown in FIGS. 3-A to 3-C and involves application to the skin of a therapeutically effective amount of each of the film forming compositions (A) and (B). The sequence of addition of composition (A) and (B) is critical for the success of the formation of hydrophilic (22) and hydrophobic (12) layers on the skin. The hydrophilic layer (22) is first spread on the surface of the skin to be treated, i.e., on the stratum corneum, in order to concentrate the moisture from the lower layers of the skin on top of and within the stratum corneum, which is the outermost skin layer. The moisture concentrates in the stratum corneum due to the hydrophilic nature of composition (A). The occlusive nature of hydrophobic composition (B) which is spread on top of the film layer (22) formed by composition (A) to form film layer 12 serves to maintain the "trapped" moisture in the stratum corneum. The hydrophobic composition (B) is generally applied immediately following application of composition (A) but may be applied as much later as up to several to tens of minutes later. Due to its high viscosity, fluidity and incompatibility with composition (A), composition (B) readily forms a layer (12) over film (22). This dual layer system thus traps and concentrates moisture in the stratum corneum.

The topical drug delivery and skin moisturizing systems of this invention are formulated using a broad spectrum of liquid hydrocarbon-terminated polymers that are clear, odor-free, non-volatile, viscous materials. The polymers vary by molecular weight, solubility, and structural characteristics and are designed to deposit and hold drugs and/or skin care agents at desired concentrations on and in the upper layers of the skin, rather than to deliver the drugs or agents into the blood stream. This skin loading approach targets skin layers so as to provide efficacy and safety advantages to dermatological products.

The topical drug delivery polymers and compositions of this invention have binding characteristics that make them resistant to accidental removal, causing them to remain on and in the upper layers of the skin for extended period of time. This binding ability thereby improves the duration of delivery of drugs or cosmetic agents.

The present polymers and compositions, when combined with pharmacological dermatological agents can reduce the amount or dosage of the dermatological agent required because the agent is directly applied to the target area. Problems with gastrointestinal irritation, absorption and metabolism encountered with oral delivery are thus avoided. The present polymers and compositions remain at or near the surface of the skin with only very low levels of penetration beyond the stratum corneum. This low systemic adsorption and low systemic toxicity of the polymers contribute to the safety of the present polymers and compositions over other delivery compounds that disrupt the skin or enter the blood stream at high levels.

However, where penetration through the stratum corneum and epidermal layers into and through the dermal layer and blood stream is desired or physiologically important, a permeation enhancing agent may be included in the drug delivery system. Examples of suitable penetration enhancers are well known in the art. Examples include those mentioned in, for example, the following U.S. patent documents: U.S. Pat. Nos. 4,867,764, 4,415,563, 3,551,554, 4,959,365, 3,989,816, 3,903,256, 3,952,099, 3,472,931, 4,557,934, 4,746,515, the disclosures of which are incorporated herein by reference thereto.

The following examples are representative of the preparation, formulation and use of the polymers and compositions of the invention.

EXAMPLE 1

To a 500 mL flask containing 45.7 g (0.174 mol) dicyclomethane-4,4'-diisocyanate and 100 mg of dibutylin dilaurate heated to 50–60° C. is added a vacuum-dried mixture of Ethoquad 18/25 (PEG-15 Stearmonium Chloride, H—$(OCH_2CH_2)_a$—$N^{\oplus}R_cR_d$—$(CH_2CH_2O)_b$, a+b=15, $R_c$=Methyl, $R_d$=n-Stearyl; Akzo Chemicals, Inc; 69.1 g, 0.0894 mol) and polyoxyethylene (20) stearyl ether (202 g, 0.176 mol). The temperature is maintained at 90° C. for 2.5 hours, after which no isocyanate is detectable.

EXAMPLE 2

The following ingredients are combined and homogenized to give a highly emollient and substantive moisturizing lotion:

| | |
|---|---|
| Water | 66.00 |
| Glycerin | 4.00 |
| Polymer of Example 1 | 2.00 |
| Arlamol E | 9.00 |
| Steareth-20 | 2.00 |
| Steareth-2 | 3.50 |
| Propylene glycol dicaprylate | 5.00 |
| Cetearyl alcohol | 3.80 |
| Decyl oleate | 4.00 |
| Germaben-II | 0.70 |

EXAMPLE 3

Using the basic procedure of Example 1 an amine-containing film-forming polymer is prepared from steareth-20, N-methyldiethanolamine, and methylenedicyclohexyl-diisocyanate.

EXAMPLES 4–6

Using the following basic procedure hydrophilic film-forming polymers are prepared from the materials indicated in the following table; where used, diols (polyethylene glycols) are added with an equivalent amount of hydrocarbyl terminated polyethylene oxide:

Eight hundred g. of polyoxyethylene compound is melted by heating to 60° C. and placed in a 1 liter glass reaction kettle fitted with mechanical stirrer and vacuum line/cold trap. With the temperature maintained at 60° C., vacuum is applied with stirring and continued until no further water collected in the cold trap. During this step the temperature is gradually raised to 100° C. The temperature is readjusted to 60° C., and 85.0 g. of 4,4'-diisocyanate and 0.4 g of stannous octoate is added; the temperature rises and within 10 minutes peaks at about 77° C. After the exotherm subsides heating is continued at 60° C. for 1.5 hour, then at 65° C. for 5 hours, until no further isocyanate is detectable. The resulting polymers are film-forming amphiphilic polymers.

|  | Hydrocarbyl terminated polyethylene oxide | Diol | Diisocyanate |
|---|---|---|---|
| Example 4 | Polyethylene glycol (m.w. 5,000) methyl ether | — | Methylenedicyclohexyl |
| Example 5 | Polyethylene glycol (m.w. 200) butyl ether | Polyethylene glycol, m.w. 8,000 | Methylenedicyclohexyl |
| Example 6 | Ethoxyethoxyethanol | Polyethylene glycol, m.w. 2,000 | Hexamethylene |

EXAMPLE 7 AND 8

Using the following basic procedure lipophilic film-forming polymers are prepared from the materials indicated in the table below; where used, polypropylene oxide (diol) is added with an equivalent amount of stearyl terminated polypropylene oxide:

A 1 L glass reaction kettle is charged with 115.4 g. of 4,4'-diisocyanate and stirring begins at room temperature. Stannous octoate (2.7 g) and hydrocarbyl terminated polypropylene oxide (320 g) are added. The temperature rises slightly to about 30° C., following which additional polypropylene oxide (500 g) and stannous octoate (1.5 g) are added. The mixture is heated to 50° C. for 1 hours, 70° C. for 1 hour, and finally at 64° C. for 5 hours, after which no further isocyanate is detectable. The resulting polymers are film-forming lipophilic polymers.

|  | Hydrocarbyl terminated polypropylene oxide | Diol | Diisocyanate |
|---|---|---|---|
| Example 7 | Polypropylene oxide (15) stearyl ether | — | Methylenedicyclohexyl |
| Example 8 | Polypropylene oxide (15) stearyl ether | Polypropylene oxide, m.w. 3,000 | Methylenedicyclohexyl |

What is claimed is:

1. A method for moisturizing skin or hair which comprises topically applying to the skin or hair an occlusive moisture barrier film-forming polymer of formula (I-a)

where $R^a$ is an alkyl of from 1 to 30 carbon atoms, alkenyl of from 2 to 30 carbon atoms or alkaryl hydrocarbyl group of from 7 to 30 carbon atoms;

Z is a divalent linking hydrocarbyl group;

$Y^1$ is O, $NR^3$ or $N^+R^3R^4X^-$ (with the proviso that when m=1 $Y^1$ is O); $Y^2$ is O, $NR^3$, $N^+R^3R^4X^-$, $(R^3NCH_2CH_2)_t$ or $\{(R^3R^4N^+CH_2CH_2)X^-\}_t$ with the proviso that $Y^1$ and $Y^2$ are not simultaneously oxygen atoms (O);

$R^3$ is a $C_1$–$C_{22}$ alkyl group; $R^4$ is a $C_1$–$C_{22}$ alkyl group;

$R^{11}$ is a methyl group or ethyl group;

$R^{12}$ is a methyl group or ethyl group;

m is 0 or 1;

n is a positive number of at least 2;

n' is a positive number of at least 2; and p is $\geq 0$; and t is a positive integer.

2. The method of claim 1 wherein $Y^1$ is O.

3. The method of claim 1 wherein in formula (I-a) $R^a$ is alkyl of from 5 to 30 carbon atoms or alkaryl of from 7 to 30 carbon atoms.

4. The method of claim 1 wherein $R^3$ and $R^4$ are alkyl groups of 10 to 22 carbon atoms.

5. The method of claim 1 which comprises topically applying a composition comprising the lipophilic film-forming polymer of formula (I-a) and at least one cosmetically active agent.

6. The method of claim 1 further comprising prior to applying the lipophilic film-forming polymer of formula (I-a) applying a layer of a hydrophilic film-forming polymer of formula (I-b1)

where Z, m, n, n' and p have the same meanings as in formula (I-a); and $R^b$ represents a short hydrocarbyl group, selected from the group consisting of $C_1$–$C_6$ alkyl and $C_{2-6}$ alkenyl; and applying the lipophilic film-forming polymer over the layer of the polymer of formula (I-b1).

7. The method of claim 1 further comprising prior to applying the lipophilic film-forming polymer of formula (I-a) applying a layer of an amphiphilic film-forming polymer of formula (I-b2)

where Z, m, n, n' and p have the same meanings as in formula (I-a); $R^1$ and $R^2$, each, independently, represent a hydrogen atom, a methyl group or an ethyl group; and $R^c$ represents a short hydrocarbyl group selected from the group consisting of $C_1$–$C_6$ alkyl and $C_2$–$C_6$ alkenyl, or $R^c$ represents a long hydrocarbyl group having from about 7 to about 30 carbon atoms, with the provisos that when $R^c$ represents said short hydrocarbyl group one of $R^1$ or $R^2$ (p≠0) is a hydrogen atom and the other is methyl group or ethyl group; and when $R^c$ represents said long hydrocarbyl group then $R^1$ and $R^2$ both represent hydrogen atoms.

8. The method of claim 7 wherein the compound of formula (I) comprises at least one lipophilic compound of formula (I-a)

where $R^a$ is an alkyl, alkenyl or alkaryl group of from 1 to 30 carbon atoms;

Z, $Y^1$, $Y^2$, m and p have the same meaning as in formula (I);

$R^{11}$ is a methyl group or ethyl group; and

$R^{12}$ is a methyl group or ethyl group;

n is a positive number of at least 2;

n' is a positive number of at least 2; and n" is a positive number of at least 2.

9. The method of claim 7 which further comprises applying at least one lipophilic polymer of formula (IV):

$$R(CO)_m O—(CH_2CHR^{12}O)_q(CO)_m R \qquad (IV)$$

wherein R and m are defined in formula (I), $R^{12}$ is defined in formula (I-a) and q is a positive number of at least 2.

10. The method of claim 1 wherein the lipophilic film-forming polymer of formula (I-a) has a molecular weight of from about 1,000 to about 30,000.

11. The method of claim 1 wherein the lipophilic film-forming polymer of formula (I-a) has a molecular weight of from about 1,000 to about 25,000.

12. The method of claim 1 wherein the lipophilic film-forming polymer of formula (I-a) has a molecular weight of from about 2,000 to about 22,000.

13. A method for facilitating the adherence of an agent applied to the skin or hair, comprising applying to the skin or hair (I) a locally administrable topical agent, and (II) a composition substantive to skin or hair and providing an occlusive moisture barrier layer when applied thereto, said composition comprising a hydrocarbon terminated urethane film-forming polymeric compound having the formula (I)

$$R—(CO)_m Y^1—(CH_2CHR^1O)_n—\{CONH—Z—NHCO(OCH_2CHR^2)_n—Y^2—(OCH_2CHR^2)_{n''}\}_p—CONH—Z—NHCO—(OCH_2CHR^1)_n—Y^1(CO)_m R \qquad (I)$$

where R represents (i) an alkyl of from 1 to 30 carbon atoms, alkenyl of from 2 to 30 carbon atoms or alkaryl group of from 7 to 30 carbon atoms or (ii) a polypropylene oxide group or polybutylene oxide group; $R^1$ and $R^2$, each, independently, represent a hydrogen atom, or a methyl or ethyl group; Z represents a divalent linking hydrocarbyl group; m is 0 or 1; when m=0, $Y^1$ represents O, $NR^3$ or $N^{\oplus}R^3R^4X^-$ and when m=1 $Y^1$ represents O; $Y^2$ represents O, $NR^3$, $N^{\oplus}R^3R^4X^-$, $(R^3NCH_2CH_2)_t$, or $\{(R^3R^4N^{\oplus}CH_2CH_2)X^-\}_t$; with the proviso that $Y^1$ and $Y^2$ are not both O at the same time; $R^3$ and $R^4$, independently, represent $C_1-C_{22}$ alkyl; X represents an anion; t is a positive integer; n and n', are each, independently, a positive number; and p is $\geq 0$.

14. The method of claim 13 wherein the compound of formula (I) comprises at least one amphiphilic or hydrophilic compound having the formula (I-b1) or (I-b2)

$$R^b(CO)_m—Y^1—(CH_2CH_2O)_n—[CONH—Z—NHCO(OCH_2CH_2)_n—Y^2—(CH_2CH_2O)_{n''}]_p—CONH—Z—NHCO—(OCH_2CH_2)_n—Y^1(CO)_m R^b \qquad (I-b1)$$

where Z, $Y^1$, $Y^2$, m, n, n', n" and p have the same meanings as in formula (I); and $R^b$ represents a short hydrocarbyl group selected from the group consisting of $C_1-C_6$ alkyl and $C_2-C_6$ alkenyl;

$$R^c—(CO)_m Y^1—(CH_2CHR^1O)_n—[CONH—Z—NHCO(OCH_2CHR^2)_n—Y^2—(CH_2CHR^2O)_{n''}]_p—CONH—Z—NHCO—(OCH_2CHR^1)_n—Y^1(CO)_m R^c \qquad (I-b2)$$

where Z, $Y^1$, $Y^2$, $R^1$, $R^2$, m, n, n' and p have the same meanings as in formula (I); and $R^c$ represents a short hydrocarbyl group selected from the group consisting of $C_1-C_6$ alkyl and $C_2-C_6$ alkenyl; or $R^c$ represents a long hydrocarbyl group having from 7 to 30 carbon atoms, with the provisos that when $R^c$ represents said short hydrocarbyl group one of $R^1$ or $R^2$ (p≠0) is a hydrogen atom and the other is methyl group or ethyl group; and when $R^c$ represents said long hydrocarbyl group then $R^1$ and $R^2$ both represent hydrogen atoms; and applying the lipophilic film-forming polymer over the layer of the polymer of formula (I-b1) or (I-b2).

15. The method of claim 14 which further comprises applying at least one hydrophilic polymer of formula (V):

$$RO—(CH_2CH_2O)_q R \qquad (V)$$

where R is defined in formula (I) and q is a positive number of at least 2.

16. The method of claim 13 wherein the film-forming polymer of formula (I) has a molecular weight of from about 1,000 to about 30,000.

17. The method of claim 13 wherein the film-forming polymer of formula (I) has a molecular weight of from about 1,000 to about 25,000.

18. The method of claim 13 wherein the film-forming polymer of formula (I) has a molecular weight of from about 2,000 to about 22,000.

* * * * *